US011268095B2

United States Patent
Zhu et al.

(10) Patent No.: US 11,268,095 B2
(45) Date of Patent: Mar. 8, 2022

(54) TREATMENT AND DIAGNOSIS OF INFLAMMATORY DISORDERS

(71) Applicants: Zhenglun Zhu, Newton, MA (US); Hong Gao, Downingtown, PA (US)

(72) Inventors: Zhenglun Zhu, Newton, MA (US); Hong Gao, Downingtown, PA (US)

(*) Notice: Subject to any disclaimer, the term of this patent is extended or adjusted under 35 U.S.C. 154(b) by 36 days.

(21) Appl. No.: 16/075,479

(22) PCT Filed: Jan. 31, 2017

(86) PCT No.: PCT/US2017/015775
§ 371 (c)(1),
(2) Date: Aug. 3, 2018

(87) PCT Pub. No.: WO2017/136322
PCT Pub. Date: Aug. 10, 2017

(65) Prior Publication Data
US 2019/0085336 A1    Mar. 21, 2019

Related U.S. Application Data

(60) Provisional application No. 62/291,271, filed on Feb. 4, 2016.

(51) Int. Cl.
| | |
|---|---|
| *C07H 21/04* | (2006.01) |
| *C12N 15/113* | (2010.01) |
| *G01N 33/50* | (2006.01) |
| *G01N 33/68* | (2006.01) |
| *C12Q 1/68* | (2018.01) |
| *C12Q 1/6883* | (2018.01) |
| *A61K 31/7115* | (2006.01) |
| *A61K 35/17* | (2015.01) |
| *C12N 5/0786* | (2010.01) |
| *A61P 29/00* | (2006.01) |

(52) U.S. Cl.
CPC ...... *C12N 15/1137* (2013.01); *A61K 31/7115* (2013.01); *A61K 35/17* (2013.01); *C12N 5/0645* (2013.01); *C12N 15/113* (2013.01); *C12Q 1/68* (2013.01); *C12Q 1/6883* (2013.01); *G01N 33/5023* (2013.01); *G01N 33/6875* (2013.01); *A61P 29/00* (2018.01); *C12N 2310/11* (2013.01); *C12N 2310/14* (2013.01); *C12N 2310/3233* (2013.01); *C12Q 2600/158* (2013.01); *G01N 2333/4703* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| | | |
|---|---|---|
| 2003/0035790 A1 | 2/2003 | Chen et al. |
| 2008/0248011 A1 | 10/2008 | Nakagawa et al. |
| 2012/0183553 A1 | 7/2012 | Zhu et al. |
| 2014/0369967 A1 | 12/2014 | Gao et al. |
| 2015/0297679 A1 | 10/2015 | Hafezi-Moghadam |

FOREIGN PATENT DOCUMENTS

| | | |
|---|---|---|
| EP | 2612675 A1 | 7/2013 |
| WO | WO-2012/071513 A2 | 5/2012 |
| WO | WO-2012/170979 A1 | 12/2012 |
| WO | WO-2014/169086 A1 | 10/2014 |

OTHER PUBLICATIONS

Corey et al. "Morpholino Antisense Oligonucleotides: Tools for Investigating Vertebrate Development" Genome Biology vol. 2, pp. 1-3, 2001.
Moretti et al. "Molecular Cloning of a Human Vent-Like Homeobox Gene" Genomics vol. 76, pp. 21-29, 2001.
Wu et al "The Homeobox Transcription Factor VentX Controls Human Macrophage Terminal Differentiation and Proinflammatory Activation" The Journal of Clinical Investigation vol. 121, pp. 2599-2613, 2011.

*Primary Examiner* — Kimberly Chong
(74) *Attorney, Agent, or Firm* — Cesari & McKenna, LLP

(57) ABSTRACT

A method of treating an inflammatory disorder in a subject, comprising administering to the subject in need thereof a nucleic acid molecule for inhibiting the expression of Hom-1. Specifically, the nucleic acid molecule is an RNAi agent or an antisense morpholino oligonucleotide. Further disclosed is a method of selecting a therapeutic for an inflammatory disorder in a subject, or monitoring the efficacy of a therapeutic for an inflammatory disorder in a subject, comprising detecting the expression level of Hom-1 in an inflamed tissue sample obtained from the subject.

4 Claims, No Drawings

Specification includes a Sequence Listing.

TREATMENT AND DIAGNOSIS OF INFLAMMATORY DISORDERS

CROSS-REFERENCE TO RELATED APPLICATIONS

This application is the National Stage of International Application No. PCT/US2017/015775, filed Jan. 31, 2017, which claims the benefit of Provisional Application No. 62/291,271, filed Feb. 4, 2016. The contents of both applications are hereby incorporated by reference in their entirety.

BACKGROUND

Tissue macrophages play major roles in host defense against pathogen invasion and in homeostasis of immunity. Plasticity is a hallmark of macrophages. Residing in a microenvironment full of signals from host cells and microbial, macrophages can be activated to display pro-inflammatory (M1) phenotype or anti-inflammatory (M2) phenotypes. Aberrant differentiation and activation of macrophages play major roles in pathogenesis of inflammation. In IBD patients for example, there is an increase of mucosal CD14+ macrophages, which display a M1 pro-inflammatory phenotype. Due to its central executor role of both innate and adaptive immunity, macrophages have been viewed as an ideal target to control autoimmune and inflammatory disorders. However, how macrophage plasticity is regulated remains incompletely understood, and the cell intrinsic factor that can be manipulated to modulate macrophage function remains largely unknown.

SUMMARY

In one aspect, described below is a method of treating an inflammatory disorder in a subject, comprising administering to a subject in need thereof a nucleic acid molecule for inhibiting the expression of Hom-1.

In one embodiment, the nucleic acid molecule is an RNAi agent or an antisense oligonucleotide. The nucleic acid molecule can be administered topically, orally, rectally, nasally, intravenously, intraarticularly, conjunctivally, intracranially, intraperitoneally, intrapleurally, intramuscularly, intrathecally, or subcutaneously. In one embodiment, the nucleic acid molecule is administered naked.

In another aspect, described herein is a composition for treating an inflammatory disorder, the composition comprising a nucleic acid molecule for inhibiting the expression of Hom-1 and a pharmaceutically acceptable carrier. In one embodiment, the nucleic acid molecule is a morpholino oligonucleotide having the sequence of SEQ ID NO: 3, 4, 5, or 6. The composition can be formulated for topical, oral, rectal, nasal, intravenous, intraarticular, conjunctival, intracranial, intraperitoneal, intrapleural, intramuscular, intrathecal, or subcutaneous route of administration. In one embodiment, the nucleic acid molecule (e.g., a morpholino oligonucleotide having the sequence of SEQ ID NO: 3, 4, 5, or 6) is a naked nucleic acid molecule.

In yet another aspect, a method of identifying a therapeutic for an inflammatory disorder is described. It includes contacting an inflamed tissue sample with a test therapeutic; and detecting the expression level of Hom-1 in the tissue sample. If the expression level is lower than or equal to a control level, the test therapeutic is a candidate therapeutic for the inflammatory disorder.

In one aspect, described below is a method of selecting a therapeutic for an inflammatory disorder in a subject in need thereof, comprising contacting an inflamed tissue sample obtained from the subject with a therapeutic; detecting a lower or same expression level of Hom-1 in the tissue sample as compared to a control level; and administering the therapeutic to the subject.

In another aspect, contemplated herein is a method of monitoring the efficacy of a therapeutic for an inflammatory disorder in a subject in need thereof, comprising detecting the expression level of Hom-1 in an inflamed tissue sample obtained from the subject after the subject has been administered with the therapeutic; comparing the detected level with a control level; and making a treatment decision based on the comparison, wherein, if the detected level is higher than the control level, continue to administer the therapeutic or a different therapeutic to the subject.

In another aspect, a method of treating an inflammatory disorder in a subject in need thereof is described herein. The method includes providing a modified macrophage, monocyte, or dendritic cell that has been treated with a Hom-1 inhibitor or contains an expression construct for expressing a Hom-1 inhibitor, wherein the modified macrophage, monocyte, or dendritic cell expresses a lower level of Hom-1 as compared with a control level; and administering an effective amount of the modified macrophage, monocyte, or dendritic cell to the subject. In one embodiment, the method includes, prior to the providing step, detecting a higher expression of Hom-1 than a control level in an inflamed tissue sample obtained from the subject.

The details of one or more embodiments are set forth in the description below. Other features, objects, and advantages of the embodiments will be apparent from the description and from the claims.

DETAILED DESCRIPTION

It was unexpectedly discovered that knocking down Hom-1 expression in tissue macrophages can abate tissue inflammation and protect viability of mucosal epithelial cells.

Hom-1, a human homeobox transcriptional factor, is an antagonist of the canonical Wnt signaling. A nucleic acid sequence of Hom-1 (SEQ ID NO: 1) and the amino acid sequence it encodes (SEQ ID NO: 2) are shown below:

```
acctggccgc catgcgcctc tcctcctccc cacctcgtgg cccgcagcag ctctccagct ttggctccgt ggactggctc tcccagagca gctgctcagg gccgaccac acccccaggc ctgccgactt ctccctgggg agcctccctg gccaggcca gacatccggc gcccgggagc cccctcaggc cgtcagcatc aaggaggccg ccgggtcctc aaatctgcct gcgccggaga ggaccatggc cgggttgagt aaggagccaa ataccttgcg ggcccccgt gtccgcacag ccttcaccat ggagcaggtc cgcaccttgg agggcgtctt ccagcaccac cagtacctga gccctctgga gcggaagagg ctggccaggg agatgcagct ctcagaggtc cagataaaaa cctggtttca gaatcgccgc atgaaacaca aacggcaaat gcaggacccc cagctgcaca gcccttctc ggggtctctc catgcgcccc cagctttcta
```

-continued

```
ctcaacgtct tctggccttg ccaatggcct gcagctgctg tgcccttggg caccectgtc cgggcccag gctctgatgc tgcccctgg ctccttctgg ggtctctgcc aagtggcaca agaggccctg gcatctgcgg gagcttcctg ctgcggcag cctctggcgt cccacccccc tacccaggc cggccttcgc tgggaccagc cctgtccacg gggccccggg gcctgtgtgc tatgccacag acgggggatg cattttgagg aggcacctct gactcccaca ctcgcggtct tgctgatcgc acctggctcc tacctggagg actcagttgt tctgtttaca tcctggtggc acctctcacc ctgacccaca caaaggttct ggagattact ggagaatata tataaatata tatatgtacg tatatatgta aatacacata tacgtatata taaatatata tatacatatg tgtgtgtata tatatatata tttttttttt tttttttttt tttgagacgg agtgttgctc tgtcacccag gctggagtgc aatgacgcaa tctcggctca ctgcaacctc cgcctcctgg gttcaagcga ttctccagcc tcagcctccc gagtagctgg gattacagac acccgccacc acgcccggct aatttttttct attttttagta gaaatggggt ttcaccatgt tagccaggct ggtctcaaac tcctgaccct gtgatccgcc cgcctcggcc tcccaaagtg ctgggattac aggcatgagc cactgcaccc ggccctgaga atatatttat taaagccacc tcttcactga aagttaccga aagagtcggt ttaggaagga aacgaagggt cagtgaacag agtcaaatgc agaagtgggc ttgtcatggg tagggctttc ggcgtacgat aaaaggatca tttgtttttt aaaagggtt ggaaaaactg gttttccagt tggaaacagt aaaggttgta agctttgtgt gtacaaaaga aaacagggaa tgcaggtgtg tttatagcgt tgtggttcaa gtccctctta acaagaactc caaagctgga aagcaggagg gaacaaaggt gaacatgaag gcgaggatgc tggggccctg cagtgcgctc taggctgtgc gtgagccggg actgtaccca cagcttgctg agggctgctc ttcttgggcc agggaaagca gggcagccgg gacctgcggc tgtgcctgga ctgaagctgt cccgcaggtc cccaccctcc aacacgtgct cacctgtccc cctcctcgca gcagcctcgg gacaaaacaa tgactcaagg acagcacttc tcgcagaagg tctggaagtg cccagaatgg gaggcacgga agccctcc ggggaggact cccgcgttga tggaccgttc ttggtgcaga ctcctgactg cgtgcatgaa acctgagaca agtgcaattc cttccatgtc gccccagagt gcccaggagg caggcagtgc ggggtgccca ggcagacggg ttcagcctgc agaactggag gcgacctgtg aaacccaccc gggcaccca acaggaacag aagcgtggtc ctgcggctgc gtcccagcg
```

```
agtttcactt tccccttgct cgtttctccc ttgttgtaag tgtttacaac tggcatgtgc ttttaaacgt caggtaagag gggaacagct gctgtacatc gtcctggcga gtgacaatgt gacagaagcc tgggcgaggc cctcggaggg cagcagctgg acaggggcta ctgggttttgg cctggacagc actgatttgt ggatgtggat gggggcacgt tgtccgtgat aaaagtacaa gtgcccctca caaaaaaaaa aaaaaaaa (SEQ ID NO: 1;

Underlined: the coding sequence)

mrlsssprg pqqlssfgsv dwlsqsscsg pthtprpadf slgslpgpgq tsgareppqa vsikeaagss nlpapertma glskepntlr aprvrtaftm eqvrtleqvf qhhqylsple rkrlaremql sevqiktwfq nrrmkhkrqm qdpqlhspfs gslhappafy stssglangl qllcpwapls gpqalmlppg sfwglcqvaq ealasagasc cgqplashpp tpgrpslgpa lstgprglca mpqtgdaf (SEQ ID NO: 2; Underlined:

aa. 91-151/homeodomain)
```

Described herein is a method of treating an inflammatory disorder in a subject in need thereof by administering to the subject a Hom-1 inhibitor, e.g., a nucleic acid molecule for inhibiting the expression of Hom-1.

The nucleic acid molecule can be an RNAi agent or an antisense oligonucelotide. In one embodiment, the nucleic acid molecule is a morpholino oligonucleotide. A morpholino oligonucleotide has the standard DNA bases (A, C, G, T) but the bases are bound to morpholine rings and linked through phosphorodiamidate groups. An anti-Hom-1 morpholino oligonucleotide can have a sequence selected from

```
                                           (SEQ ID NO: 3)
     5'-TACTCAACCCTGACATAGAGGGTAA-3, (SEQ ID NO: 4)
     5'-GAGCCCGGTTTGCATACACGGCTAA-3', (SEQ ID NO: 5)
     5'-GCCCAGATAAGCAGCGCCTAATTGC-3',
     and (SEQ ID NO: 6)
     5'-CTGTAGGAAAAGCAAGATCAGAACA-3'.
```

The term "RNAi agent" refers to an RNA (or analog thereof), having sufficient sequence complementarity to a target RNA to direct RNA interference. Generally, an interfering RNA ("iRNA") is a double stranded short-interfering RNA (siRNA) or short hairpin RNA (shRNA) that results in catalytic degradation of specific mRNAs. An antisense oligonucleotide is typically a single-stranded DNA, RNA, or an analog thereof that has a sequence that can bind to a target nucleic acid molecule.

The anti-Hom-1 nucleic acid molecule can be administered to the subject via any route of administration, e.g., topical, oral, rectal, nasal, intravenous, intraarticular, conjunctival, intracranial, intraperitoneal, intrapleural, intramuscular, intrathecal, or subcutaneous route of administration. The route can be selected based on the site of inflammation. A pharmaceutical composition containing an anti-Hom-1 nucleic acid molecule can be formulated for any route of administration, e.g., as an injectable solution, pill, capsule, eye drop, spray, inhaler, topical cream or gel, or aerosol).

In one embodiment, the anti-Hom-1 nucleic acid molecule is administered naked. In other words, no delivery vehicles such as liposomes or viral vectors are used with the nucleic acid molecule.

Prior to the administration of any Hom-1 inhibitor to a subject, the subject can be tested to determine whether he or she has an elevated expression level of Hom-1 and/or an elevated expression level of an inflammatory cytokine as compared to a control level. In one embodiment, the expression level is detected in an inflamed tissue sample obtained from the subject. A subject with an increased expression level of Hom-1 can be treated with a Hom-1 inhibitor. A control level can be a level representative of the Hom-1 expression level in a non-inflamed tissue or subjects without inflammatory disorders, or a level found in a non-inflamed tissue in the subject to be treated.

A "subject" refers to a human and a non-human animal. "Treating" or "treatment" refers to administration of a compound or agent to a subject, who has a disorder, with the purpose to cure, alleviate, relieve, remedy, delay the onset of, or ameliorate the disorder, the symptom of the disorder, the disease state secondary to the disorder, or the predisposition toward the disorder. An "effective amount" refers to an amount of the compound that is capable of producing a medically desirable result in a treated subject. The treatment method can be performed alone or in conjunction with other drugs or therapy.

Also described herein is a screening method of identifying a therapeutic for an inflammatory disorder. The method includes contacting an inflamed tissue sample with a test therapeutic and detecting the expression level of Hom-1 in the tissue sample. If the expression level is lower than or equal to a control level, the test therapeutic is a candidate therapeutic for the inflammatory disorder.

A method of selecting a therapeutic for an inflammatory disorder in a subject in need thereof is also described. The method includes contacting an inflamed tissue sample obtained from the subject with a therapeutic, detecting a lower or same expression level of Hom-1 in the tissue sample as compare to a control level, and administering the therapeutic to the subject.

Further described is a method of monitoring the efficacy of a therapeutic for an inflammatory disorder in a subject in need thereof. The method includes detecting the expression level of Hom-1 in an inflamed tissue sample obtained from the subject after the therapeutic is administered to the subject, comparing the detected level with a control level, and making a treatment decision based on the comparison. If the detected level is lower than the control level, it indicates that the therapeutic is effective for treating inflammation in the subject. If the detected level is the same as or higher than the control level, a decision can be made to continue giving the same therapeutic or to try a different therapeutic.

The therapeutic or test therapeutic can be a protein, peptide, peptidomimetic, peptoid, cell, antibody or fragment thereof, small molecule compound, nucleic acid molecule, or a plant extract. In one embodiment, the therapeutic or test therapeutic can be a steroid, non-steroidal anti-inflammatory drug, or immuno-suppressant.

In the above-described screening, selecting or monitoring method, the control level can be a level representative of the expression level of Hom-1 in a non-inflamed tissue. It can also be the expression level of Hom-1 in the inflamed tissue sample before it was contacted with a therapeutic or test therapeutic. A skilled person would be able to determine suitable control levels.

In one aspect, a method of treating an inflammatory disorder using modified macrophages, monocytes, or dendritic cells is described. The method includes providing modified macrophages, monocytes, or dendritic cells that have been treated with a Hom-1 inhibitor or contain an expression construct for expressing a Hom-1 inhibitor. The modified macrophages, monocytes, or dendritic cells express a lower level of Hom-1 as compared with a control level. An effective amount of the modified macrophages, monocytes, or dendritic cells are administered to a subject with an inflammatory disorder.

The Hom-1 inhibitor can be a protein, peptide, peptidomimetic, peptoid, cell, antibody or fragment thereof, small molecule compound, nucleic acid molecule, or a plant extract. In one embodiment, the inhibitor is an RNAi agent or an antisense oligonucleotide (e.g., a morpholino oligonucleotide).

Prior to administering the modified cells to a subject, the expression level of Hom-1 in a sample (e.g., an inflamed tissue sample) obtained from the subject can be determined. If the expression level is higher than a control level, the subject is deemed as suitable for the treatment. The control level can be a level representative of the level in a non-inflamed tissue or the level detected in a non-inflamed tissue sample obtained from the subject to be treated. Again, a skilled practitioner would be able to determine a suitable control level.

Hom-1 expression level can be determined at either the mRNA level or at the protein level. Methods of measuring mRNA levels and protein levels are well known in the art.

In any of the methods described herein, in addition to or alternatively to detecting the expression level of Hom-1 as an indicator of inflammation (e.g., the presence or degree of inflammation), detecting the expression and/or secretion of a pro-inflammatory cytokine, the expression and/or secretion of an anti-inflammatory cytokine, the expression of a marker of M1 or M2 macrophages, the expression of a marker of DC differentiation and activation can also be used to measure inflammation.

An inflammatory disorder is characterized by a local or systemic, acute, or chronic inflammation. Inflammatory disorders include, but are not limited to, inflammatory dermatoses (e.g., dermatitis, psoriasis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, or eosinophilic fasciitis), inflammatory bowel diseases (e.g., Crohn's disease and ulcerative colitis), acute respiratory distress syndrome, fulminant hepatitis, pancreatitis, hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, COPD, allergic rhinitis, rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, multiple sclerosis, primary lateral sclerosis, amyotrophic lateral sclerosis, anaphylaxia, systemic anaphylaxia, hypersensitivity responses, systemic inflammatory conditions, drug allergies, insect sting allergies, allograft rejection, graft-versus-host disease, Sjogren's syndrome, human immunodeficiency, a virus infection, atherosclerosis, hypertension, diabetes, and chronic renal diseases, ocular inflammatory diseases, uveitis and conjunctivitis, neuritis.

A skilled practitioner would be able to determine whether a person has an inflammatory disorder. The expression level of Hom-1 in a sample (e.g., a tissue, cell or bodily fluid sample) obtained from a subject suspected of having an inflammatory disorder can also be used as a diagnostic tool.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent.

EXAMPLE

Macrophages are key regulators of both innate and adaptive immunity. How macrophage plasticity is regulated by cell intrinsic factors is incompletely understood. The data described below demonstrate that the human homeobox transcription factor, Hom-1, plays a pivotal role in directing macrophage polarization towards the M1 phenotype. Hom-1 expression is aberrantly elevated in tissue macrophages isolated from inflamed mucosa of IBD patients. Using an en bloc culture model, we showed that knockdown of Hom-1 expression in tissue macrophages by morpholigo oligonucleotides can abate tissue inflammation and protect viability of mucosal epithelial cells. Taken together, our data suggest that Hom-1 can serve as a novel target to manage inflammatory disorders.

Hom-1 Expression is Up-Regulated in Macrophages Isolated from Inflamed Gastrointestinal Mucosa Using an in vitro monocyte-derived macrophage model, we showed that Hom-1 controls monocytes to macrophage differentiation and pro-inflammatory activation. To explore the potential role of Hom-1 in tissue macrophage differentiation and activation, we examined Hom-1 expression in mucosal macrophages isolated from mucosa of IBD patients. We found that Hom-1 expression was significantly elevated in macrophages isolated from inflamed mucosa, in comparison to the control macrophages isolated from normal mucosa of the same patients. Using FACAS and ELISA analysis, we found that, in parallel to the elevated expression of Hom-1, the expression of M1 surface markers, such as CD40, CD80, and CD86 as well as the expression and secretion of M1 pro-inflammatory cytokines were elevated in macrophages isolate from inflamed mucosa. In addition, we found that the expression of reactive oxygen species (ROS) and Nitric oxide (NO) were also elevated in macrophages isolated from inflamed mucosa.

Hom-1 Regulates Mucosal Macrophage Plasticity and Polarizes Mucosal Macrophage Towards M1 Phenotype Plasticity is a hall mark of macrophages. In response to environmental cues, macrophages display spectrums of phenotypes, ranging from the classic pro-inflammatory M1 phenotype to a variety of M2 phenotypes with distinguished features. Corticosteroids have been used extensively to manage inflammatory disorders and have been shown to induce M2 phenotype of macrophages. To determine whether Hom-1 plays a role in regulating mucosal macrophage plasticity, we examined the effects of Corticosteroids on the expression of Hom-1. Incubation of mucosal CD14 macrophages with predinisolone led to a significant reduced level of Hom-1 expression and a characteristic reduced secretion of M1 cytokines IL12, but an increased secretion of M2 cytokine IL10. Consistent with a potential role of Hom-1 in regulating macrophage plasticity, we found that the morphologies of GFP transfected but not the GFP-Hom-1 transfected mucosal macrophages can be induced by PD to display characteristic roundup phenotypes. FACS analysis of cell surface expression of CD80 and ELISA analysis of secretion of IL12 culture media in GPF or GFP-Hona-1 expressing macrophages showed that Hom-1 rendered the macrophages resistant to PD induced reduction of CD80 and secretion of IL12. To further explore whether Hom-1 regulates macrophage polarization, we examined Hom-1 expression during induced M2 to M1 switch, using the in vitro macrophage differentiation model as previously described. We found that Hom-1 expression is elevated during induced M2 to M1 polarization. To define a key regulatory role of Hom-1 in polarization of macrophages, we examined the effects of knocking-down Hom-1 in LPS-induced M2 to M1 phenotype switch. We found that down-regulation of Hom-1 renders macrophages resistant to the LPS induced M1 polarization, suggesting a key regulatory role of Hom-1 in the process. To further define the function of Hom-1 in macrophage polarization, we explored the effects of ectopic expression of Hom-1 in M2 macrophages and found that over expression of Hom-1 led to a significant increase of surface expression of M1 marker, CD 80 as well as elevated secretion of M1 cytokines, IL1b, IL12 and TNFa. Taken together, the data suggested that Hom-1 plays a key role in regulating macrophages plasticity and polarizes macrophages towards M1 phenotype.

Hom-1 Differentially Regulates the Expression of M1 and M2 Genes

To explore the potential mechanisms of Hom-1 regulated polarization of macrophages, we examined the effects of ectopic expression of Hom-1 on the expression characteristic M1 and M2 genes. We found that Hom-1 expression promotes the expression of M1 genes, such as ILL IL12 and TNFa, but suppresses the expression of M2 genes, such as IL10 and TGFb. Together with our previous findings that Hom-1 expression is required for the expression of M1 genes, such not the expression of tested M2 genes, our data suggested that Hom-1 regulates macrophage plasticity through polarizing the expression of M1 and M2 genes.

Targeting Hom-1-Regulated Macrophage Plasticity in Pathogenesis of Tissue Inflammation To further determine whether Hom-1-regulated macropahges can be targeted to abate tissue inflammation, we used en bloc culture of tissues obtained from inflamed or normal mucosa of ulcerative colitis (UC) patients. We found that, consistent with clinical findings, the secretion of inflammatory cytokines, such as TNFa, IL1β and Nitrate was significantly elevated in the culture of inflamed tissues. We then added anti-Hom-1 morpholino oligonucleotides (MO) to the tissue cultures and examined whether it can down-regulate the expression of Hom-1 in mucosal macrophages. We found that Hom-1 Mo efficiently inhibited Hom-1 expression in macrophages in the en bloc tissue cultures. To further explore the effect of Hom-1 MO on tissue inflammation, we examined the concentrations of TNFa during the incubation of en bloc tissue with Hom-1, using ELISA assay. We found that Hom-1 MO reduced the amount of TNFa in the cultures in a dosage dependent manner. To further explore the effects of Hom-1 MO on the secretion of other pro-inflammatory cytokines, we examined the effects of Hom-1 MO on the secretion of IL1 and Nitrate and found that, similar to the TNFa, Hom-1 MO exerts strong inhibition of these pro-inflammatory cytokines in the en bloc culture systems. As the ex-vivo en bloc culture may reflect the tissue microenvironment in vivo, our data suggested that Hom-1 MO can target tissue macrophages to abate tissue inflammation.

Hom-1 MO Rescue Viability of Epithelial Cells in Inflamed Tissue Inflammation

Apoptosis of epithelial cells, which causes mucosal ulceration, is a hallmark of IBD. Tissue inflammation has been thought to be the major trigger of apoptosis of mucosal epithelial cells. Using en bloc tissue culture, we found that there was a greater rate of apoptosis of mucosal epithelial cells in tissues isolated from inflamed mucosa in comparison to the apoptotic rate of epithelial cells in normal control tissue. When Hom-1 MO was added to the en bloc tissue culture, we found that Hom-1 MO but not the control MO exerted strong inhibitory effects on apoptosis of epithelial cells in tissue culture. Taken together with our findings that Hom-1 MO can abate tissue inflammation, the data suggested that Hom-1 MO can function as an agent to manage inflammation.

Monocytes Isolation and Culture

Peripheral blood mononuclear cells (PBMC) from healthy adult donors at Children's Hospital Boston were isolated by Ficoll density gradient centrifugation. Experiments with human materials were performed in accordance with guidelines approved by the institutional review committee of Brigham and Women's Hospital. CD14$^+$ monocytes were purified from PBMCs using anti-CD14-coated microbeads (Miltenyi Biotec). The purity of freshly isolated CD14$^+$ monocytes was more than 95% as analyzed by flow cytometry. Monocytes were cultured in 12-well plates at $1\times10^6$ cells/ml with RPMI 1640 medium containing 10% fetal bovine serum (FBS). M-CSF, GM-CSF, and IL3 were purchased from PeproTech and used at the final concentration of 100 ng/ml. Cytokines were added to cultures every 2 or 3 days.

RNA Interference

Human primary monocytes were transfected using the Human Monocyte Nucleofector Kit (Lonza) according to the manufacturer's instructions. Briefly, $5\times10^6$ monocytes were resuspended into 100 µl nucleofector solution with 0.5 nmol of either Hom-1 siRNA (forward: 5'-UUCAGAAUCGCCG-CAUGAAACACAAACGG-3' (SEQ ID NO: 7); reverse: 5'-CCGUUUGUGUUUCAUGCGGCGAUUCUGAA-3' (SEQ ID NO: 8)) or non-effective GFP siRNA (forward: 5'-UGACCACCCUGACCUACGGCGUGCAGUGC-3' (SEQ ID NO: 9); 5'-reverse: GCACUGCACGCCGUAG-GUCAGGGUGGUCA-3' (SEQ ID NO: 10)) before electroporation with nucleofector II Device (Lonza). Cells were then immediately removed from the device and incubated overnight with 1 ml pre-warmed Human Monocyte Nucleofector Medium containing 2 mM glutamine and 10% FBS. Cells were then resuspended into complete RPMI medium and treated with appropriate cytokines to induce differentiation into macrophages. Similarly, macrophages derived from monocytes were transfected with Human Macrophage Nucleofector Kit (Lonza) following the manufacturer's instructions.

FACS Analysis

Phenotypic analysis of monocytes/macrophages was performed using flow cytometry after immunolabeling of cells with fluorescence dye conjugated antibodies. The following antibodies were used: PE-conjugated anti-CD71, CD11b, CD11c, CD16, CD64, CD80, CD86, HLA-DR, CD14, TLR4, IL1-β and TNF-α, and FITC-conjugated anti-CD40, CD36 (eBioscience); FITC-conjugated anti-mannose receptor (MR), and unconjugated mouse anti-MCSFR (R&D Systems). Isotype control labeling was performed in parallel. Antibodies were diluted as recommended by the supplier. PE-conjugated rabbit against mouse IgG antibody was used for secondary M-CSFR staining Labeled cells were analyzed with FACScan flow cytometer (BD Bioscience) using CellQuest software. Results are expressed as the percentage of positive cells and/or mean fluorescence intensity (MFI) values after subtraction of the MFI obtained with the isotype control antibody.

RT-PCR

Total RNA was isolated by the TRIzol reagent, and an equal amount of RNA was used for first-strand cDNA synthesis with SuperScript III First-Strand Synthesis System (Invitrogen) according to the manufacturer's protocol. To amplify Hom-1 cDNA with conventional PCR, AccuPrime™ Taq DNA polymerase system (Invitrogen) was used following the manufacturer's instructions. PCR products were separated on 2% agarose gels and stained with ethidium bromide. GAPDH was used as an internal control. We performed quantitative measurement of Hom-1 and cytokines cDNA with SYBR Green on a LightCycler® (480 Real-Time PCR System; Roche).

Cytokine Measurements

Levels of IL-1β and TNF-α and IL12p70 in the supernatants of E. coli LPS (Sigma) and IFN-γ (PeproTech) treated macrophage or LPS treated U937 cells were quantified using ELISA kits obtained from eBiosciences. Analyses were conducted according to the manufacturer's instructions.

Detection of Reactive Oxygen Species (ROS) and Nitric Oxide (NO)

The ROS level in activated macrophages was detected with Image-iT® LIVE Green Reactive Oxygen Species Detection Kit (Invitrogen) basically following the manufacturer's instructions except that the results were analyzed by both fluorescence microscope and flow cytometry. The NO level was determined by Griess Reagent Kit for Nitrite Determination (Invitrogen) following the protocol provided by the manufacturer.

Cytostaining

For Wright-Giemsa staining, a staining kit from Sigma was used according to the manufacturer's instructions.

Statistical Analysis

Data were analyzed using the paired Student's t test (2-tailed) and Wilcoxon rank-sum test. The differences with p value <0.05 were considered statistically significant.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A method of treating an inflammatory disorder in a subject in need thereof, comprising:
   providing a modified macrophage, monocyte, or dendritic cell that has been treated with a Hom-1 inhibitor or contains an expression construct for expressing a Hom-1 inhibitor, wherein the modified macrophage, monocyte, or dendritic cell expresses a lower level of Hom-1 as compared with a control level, the Hom-1 inhibitor being an RNAi agent or an antisense oligonucleotide; and
   administering an effective amount of the modified macrophage, monocyte, or dendritic cell to the subject.

2. The method of claim 1, wherein the Hom-1 inhibitor inhibits the expression of Hom-1.

3. The method of claim 2, wherein the Hom-1 inhibitor is a morpholino oligonucleotide.

4. The method of claim 1, further comprising, prior to the providing step, detecting a higher expression of Hom-1 than a control level in an inflamed tissue sample obtained from the subject.

* * * * *

SEQUENCE LISTING

<160> NUMBER OF SEQ ID NOS: 10

<210> SEQ ID NO 1
<211> LENGTH: 2428
<212> TYPE: DNA
<213> ORGANISM: Homo sapiens
<220> FEATURE:
<221> NAME/KEY: CDS
<222> LOCATION: (12)..(788)
<223> OTHER INFORMATION: Hom-1

<400> SEQUENCE: 1

```
acctggccgc c atg cgc ctc tcc tcc tcc cca cct cgt ggc ccg cag cag      50
            Met Arg Leu Ser Ser Ser Pro Pro Arg Gly Pro Gln Gln
             1               5                  10 ctc tcc agc ttt ggc tcc gtg gac tgg ctc tcc cag agc agc tgc tca       98
Leu Ser Ser Phe Gly Ser Val Asp Trp Leu Ser Gln Ser Ser Cys Ser
    15                  20                  25 ggg ccg acc cac acc ccc agg cct gcc gac ttc tcc ctg ggg agc ctc      146
Gly Pro Thr His Thr Pro Arg Pro Ala Asp Phe Ser Leu Gly Ser Leu
30                  35                  40                  45 cct ggc cca ggc cag aca tcc ggc gcc cgg gag ccc cct cag gcc gtc      194
Pro Gly Pro Gly Gln Thr Ser Gly Ala Arg Glu Pro Pro Gln Ala Val
                50                  55                  60 agc atc aag gag gcc gcc ggg tcc tca aat ctg cct gcg ccg gag agg      242
Ser Ile Lys Glu Ala Ala Gly Ser Ser Asn Leu Pro Ala Pro Glu Arg
            65                  70                  75 acc atg gcc ggg ttg agt aag gag cca aat acc ttg cgg gcc ccc cgt      290
Thr Met Ala Gly Leu Ser Lys Glu Pro Asn Thr Leu Arg Ala Pro Arg
        80                  85                  90 gtc cgc aca gcc ttc acc atg gag cag gtc cgc acc ttg gag ggc gtc      338
Val Arg Thr Ala Phe Thr Met Glu Gln Val Arg Thr Leu Glu Gly Val
    95                 100                 105 ttc cag cac cac cag tac ctg agc cct ctg gag cgg aag agg ctg gcc      386
Phe Gln His His Gln Tyr Leu Ser Pro Leu Glu Arg Lys Arg Leu Ala
110                 115                 120                 125 agg gag atg cag ctc tca gag gtc cag ata aaa acc tgg ttt cag aat      434
Arg Glu Met Gln Leu Ser Glu Val Gln Ile Lys Thr Trp Phe Gln Asn
                130                 135                 140 cgc cgc atg aaa cac aaa cgg caa atg cag gac ccc cag ctg cac agc      482
Arg Arg Met Lys His Lys Arg Gln Met Gln Asp Pro Gln Leu His Ser
            145                 150                 155 ccc ttc tcg ggg tct ctc cat gcg ccc cca gct ttc tac tca acg tct      530
Pro Phe Ser Gly Ser Leu His Ala Pro Pro Ala Phe Tyr Ser Thr Ser
        160                 165                 170 tct ggc ctt gcc aat ggc ctg cag ctg ctg tgc cct tgg gca ccc ctg      578
Ser Gly Leu Ala Asn Gly Leu Gln Leu Leu Cys Pro Trp Ala Pro Leu
    175                 180                 185 tcc ggg ccc cag gct ctg atg ctg ccc cct ggc tcc ttc tgg ggt ctc      626
Ser Gly Pro Gln Ala Leu Met Leu Pro Pro Gly Ser Phe Trp Gly Leu
190                 195                 200                 205 tgc caa gtg gca caa gag gcc ctg gca tct gcg gga gct tcc tgc tgc      674
Cys Gln Val Ala Gln Glu Ala Leu Ala Ser Ala Gly Ala Ser Cys Cys
                210                 215                 220 ggg cag cct ctg gcg tcc cac ccc cct acc cca ggc cgg cct tcg ctg      722
Gly Gln Pro Leu Ala Ser His Pro Pro Thr Pro Gly Arg Pro Ser Leu
            225                 230                 235 gga cca gcc ctg tcc acg ggg ccc cgg ggc ctg tgt gct atg cca cag      770
Gly Pro Ala Leu Ser Thr Gly Pro Arg Gly Leu Cys Ala Met Pro Gln
        240                 245                 250 acg ggg gat gca ttt tga ggaggcacct ctgactccca cactcgcggt             818
Thr Gly Asp Ala Phe
```

Thr Gly Asp Ala Phe
    255

```
cttgctgatc gcacctggct cctacctgga ggactcagtt gttctgttta catcctggtg    878
gcacctctca ccctgaccca cacaaaggtt ctggagatta ctggagaata tatataaata    938
tatatatgta cgtatatatg taaatacaca tatacgtata tataaatata tatatacata    998
tgtgtgtgta tatatatata tattttttt ttttttttt ttttgagac ggagtgttgc      1058
tctgtcaccc aggctggagt gcaatgacgc aatctcggct cactgcaacc tccgcctcct   1118
gggttcaagc gattctccag cctcagcctc ccgagtagct gggattacag cacccgcca    1178
ccacgcccgg ctaattttt ctatttttag tagaaatggg gtttcaccat gttagccagg    1238
ctggtctcaa actcctgacc ctgtgatccg cccgcctcgg cctcccaaag tgctgggatt   1298
acaggcatga gccactgcac ccggccctga aatatatttt attaaagcca cctcttcact   1358
gaaagttacc gaaagagtcg gtttaggaag gaaacgaagg gtcagtgaac agagtcaaat   1418
gcagaagtgg gcttgtcatg gtagggctt tcggcgtacg ataaaaggat catttgtttt    1478
ttaaagggg ttggaaaaac tggttttcca gttggaaaca gtaaaggttg taagctttgt    1538
gtgtacaaaa gaaacagggg aatgcaggtg tgtttatagc gttgtggttc aagtccctct   1598
taacaagaac tccaaagctg gaaagcagga gggaacaaag gtgaacatga aggcgaggat   1658
gctgggccc tgcagtgcgc tctaggctgt gcgtgagccg ggactgtacc cacagcttgc    1718
tgagggctgc tcttcttggg ccagggaaag cagggcagcc gggacctgcg gctgtgcctg   1778
gactgaagct gtcccgcagg tccccaccct ccaacacgtg ctcacctgtc ccctcctcg    1838
cagcagcctc gggacaaaac aatgactcaa ggacagcact tctcgcagaa ggtctggaag   1898
tgcccagaat gggaggcacg gaagcccctc ccggggagga ctcccgcgtt gatggaccgt   1958
tcttggtgca gactcctgac tgcgtgcatg aaacctgaga caagtgcaat tccttccatg   2018
tcgccccaga gtgcccagga ggcaggcagt gcggggtgcc caggcagacg ggttcagcct   2078
gcagaactgg aggcgacctg tgaaacccac ccgggcaccc aacaggaac agaagcgtgg    2138
tcctgcggct gcgtcccag cgagtttcac tttcccctg ctcgtttctc ccttgttgta     2198
agtgtttaca actggcatgt gcttttaaac gtcaggtaag aggggaacag ctgctgtaca   2258
tcgtcctggc gagtgacaat gtgacagaag cctgggcgag ccctcggag gcagcagct    2318
ggacaggggc tactgggttt ggcctggaca gcactgattg tgatgtgg atgggggcac    2378
gttgtccgtg ataaaagtac aagtgcccct cacaaaaaaa aaaaaaaaa              2428
```

<210> SEQ ID NO 2
<211> LENGTH: 258
<212> TYPE: PRT
<213> ORGANISM: Homo sapiens

<400> SEQUENCE: 2

Met Arg Leu Ser Ser Ser Pro Arg Gly Pro Gln Gln Leu Ser Ser
1               5                   10                  15

Phe Gly Ser Val Asp Trp Leu Ser Gln Ser Ser Cys Ser Gly Pro Thr
            20                  25                  30

His Thr Pro Arg Pro Ala Asp Phe Ser Leu Gly Ser Leu Pro Gly Pro
        35                  40                  45

Gly Gln Thr Ser Gly Ala Arg Glu Pro Pro Gln Ala Val Ser Ile Lys
    50                  55                  60

Glu Ala Ala Gly Ser Ser Asn Leu Pro Ala Pro Glu Arg Thr Met Ala
65                  70                  75                  80

```
Gly Leu Ser Lys Glu Pro Asn Thr Leu Arg Ala Pro Arg Val Arg Thr
                85                  90                  95

Ala Phe Thr Met Glu Gln Val Arg Thr Leu Glu Gly Val Phe Gln His
            100                 105                 110

His Gln Tyr Leu Ser Pro Leu Glu Arg Lys Arg Leu Ala Arg Glu Met
        115                 120                 125

Gln Leu Ser Glu Val Gln Ile Lys Thr Trp Phe Gln Asn Arg Arg Met
130                 135                 140

Lys His Lys Arg Gln Met Gln Asp Pro Gln Leu His Ser Pro Phe Ser
145                 150                 155                 160

Gly Ser Leu His Ala Pro Pro Ala Phe Tyr Ser Thr Ser Ser Gly Leu
                165                 170                 175

Ala Asn Gly Leu Gln Leu Leu Cys Pro Trp Ala Pro Leu Ser Gly Pro
            180                 185                 190

Gln Ala Leu Met Leu Pro Pro Gly Ser Phe Trp Gly Leu Cys Gln Val
        195                 200                 205

Ala Gln Glu Ala Leu Ala Ser Ala Gly Ala Ser Cys Cys Gly Gln Pro
    210                 215                 220

Leu Ala Ser His Pro Pro Thr Pro Gly Arg Pro Ser Leu Gly Pro Ala
225                 230                 235                 240

Leu Ser Thr Gly Pro Arg Gly Leu Cys Ala Met Pro Gln Thr Gly Asp
                245                 250                 255

Ala Phe

<210> SEQ ID NO 3
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 3
tactcaaccc tgacatagag ggtaa                                              25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
gagcccggtt tgcatacacg gctaa                                              25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
gcccagataa gcagcgccta attgc                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 6
ctgtaggaaa agcaagatca gaaca                                                 25

<210> SEQ ID NO 7
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 7
uucagaaucg ccgcaugaaa cacaaacgg                                             29

<210> SEQ ID NO 8
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 8
ccguuugugu uucaugcggc gauucugaa                                             29

<210> SEQ ID NO 9
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 9
ugaccacccu gaccuacggc gugcagugc                                             29

<210> SEQ ID NO 10
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 10
gcacugcacg ccguaggguca ggguggguca                                           29
```